US00PP31299P2

(12) United States Plant Patent
Bak et al.

(10) Patent No.: US PP31,299 P2
(45) Date of Patent: Dec. 31, 2019

(54) ***MEDINILLA* HYBRID PLANT NAMED 'ROYAL GLOW'**

(50) Latin Name: ***Medinilla* hybrid**
Varietal Denomination: ROYAL GLOW

(71) Applicants: Elly Bak, Rijsenhout (NL); Nicolaas D. M. Steur, Oude Niedorp (NL)

(72) Inventors: Elly Bak, Rijsenhout (NL); Nicolaas D. M. Steur, Oude Niedorp (NL)

(73) Assignee: Corn Bak BV (NL)

( * ) Notice: Subject to any disclaimer, the term of this patent is extended or adjusted under 35 U.S.C. 154(b) by 0 days.

(21) Appl. No.: 15/932,938

(22) Filed: May 22, 2018

(51) Int. Cl.
*A01H 5/02* (2018.01)

(52) U.S. Cl.
USPC ..... Plt./226

(58) Field of Classification Search
USPC ..... Plt./263.1, 226
CPC ..... A01H 6/00; A01H 5/02
See application file for complete search history.

*Primary Examiner* — Keith O. Robinson
(74) *Attorney, Agent, or Firm* — Cassandra Bright

(57) ABSTRACT

A new and distinct *Medinilla* cultivar named 'ROYAL GLOW' is disclosed, characterized by a solid growth habit, erect plant habit, measuring about 35 cm in height; green colored leaves, and pendulous panicles with red-purple (RHS 63B) colored flowers. The new variety is a *Medinilla*, normally produced as an ornamental plant.

2 Drawing Sheets

Latin name of the genus and species: *Medinilla* hybrid.
Variety denomination: 'ROYAL GLOW'.

BACKGROUND OF THE INVENTION

The present invention relates to a new and distinct hybrid cultivar of *Medinilla* plant, botanically known as *Medinilla* hybrid, hereinafter referred to by the cultivar name 'ROYAL GLOW'. The genus of *Medinilla* belongs to the Melastomataceae family.

The new *Medinilla* 'ROYAL GLOW' is a product of a planned breeding program conducted by the inventors, Elly Bak and Nico D. M. Steur, in Assendelft, The Netherlands. The seed parent is the *Medinilla* selection designated '88078319' (unpatented). The pollen parent is the *Medinilla* selection designated '88078320' (unpatented). The objective of the breeding program was to produce a new *Medinilla* variety with good growing habits and an attractive inflorescence. The crossing was made in 2011.

'ROYAL GLOW' was discovered and selected by the inventors in 2013, as a single flowering plant, at a research greenhouse in Assendelft, The Netherlands.

Asexual reproduction of the new *Medinilla* hybrid 'ROYAL GLOW' terminal vegetative stem cuttings was first performed in 2013 Assenfeldt, the Netherlands. Subsequent propagation has demonstrated that the combination of characteristics as herein disclosed for the new cultivar are firmly fixed and retained through successive generations of asexual reproduction. The new cultivar reproduces true-to-type.

BRIEF DESCRIPTION OF THE INVENTION

The following traits have been repeatedly observed and are determined to be the unique characteristics of 'ROYAL GLOW' which in combination distinguish this *Medinilla* hybrid as a new and distinct cultivar:

1. Solid growth habit;
2. Erect shrub plant, measuring about 35 cm in height (above the pot when first flowering);

3. Green colored leaves, measuring about 25 cm in length and about 13 cm in width;
4. Pendulous panicles with red-purple (RHS 63B) colored flowers.

COMMERCIAL COMPARISON

Of the commercial cultivars known to the present inventors, the most similar in comparison to the new *Medinilla* 'ROYAL GLOW' is the *Medinilla* 'ROYAL INTENZ'(U.S. Plant Pat. No. 26,665). Plants of the new *Medinilla* 'ROYAL GLOW' differ from the plants of *Medinilla* 'ROYAL INTENZ' in the following ways:

1. Plants of 'ROYAL GLOW' have smaller leaves than plants of 'ROYAL INTENZ'.
2. Plants of 'ROYAL GLOW' have lighter colored inflorescences than 'ROYAL INTENZ'.

BRIEF DESCRIPTION OF THE PHOTOGRAPHS

The accompanying photograph illustrates the overall appearance of the new *Medinilla* 'ROYAL GLOW' showing the colors as true as is reasonably possible with colored reproductions of this type. Colors in the photograph may differ slightly from the color values cited in the detailed botanical description which accurately describes the color of 'ROYAL GLOW'.

Figure 1:
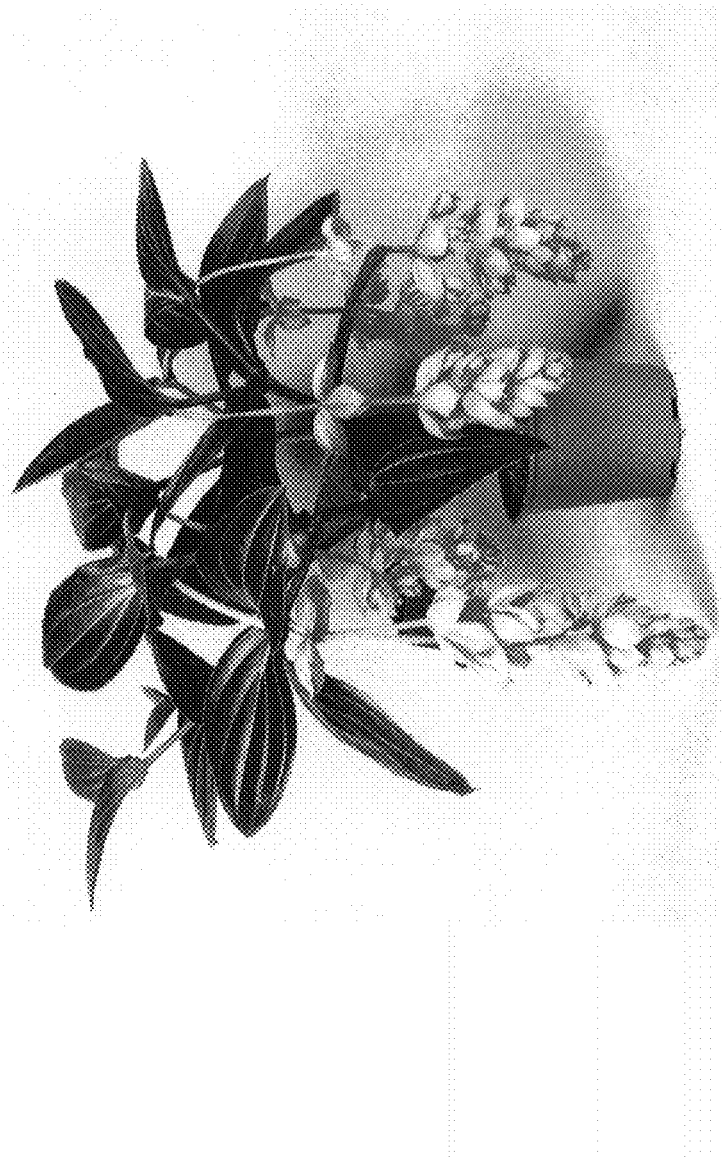

FIG. 1. shows a side view perspective of a typical potted flowering plant of 'ROYAL GLOW' at about 50 weeks from potting.

Figure 2:
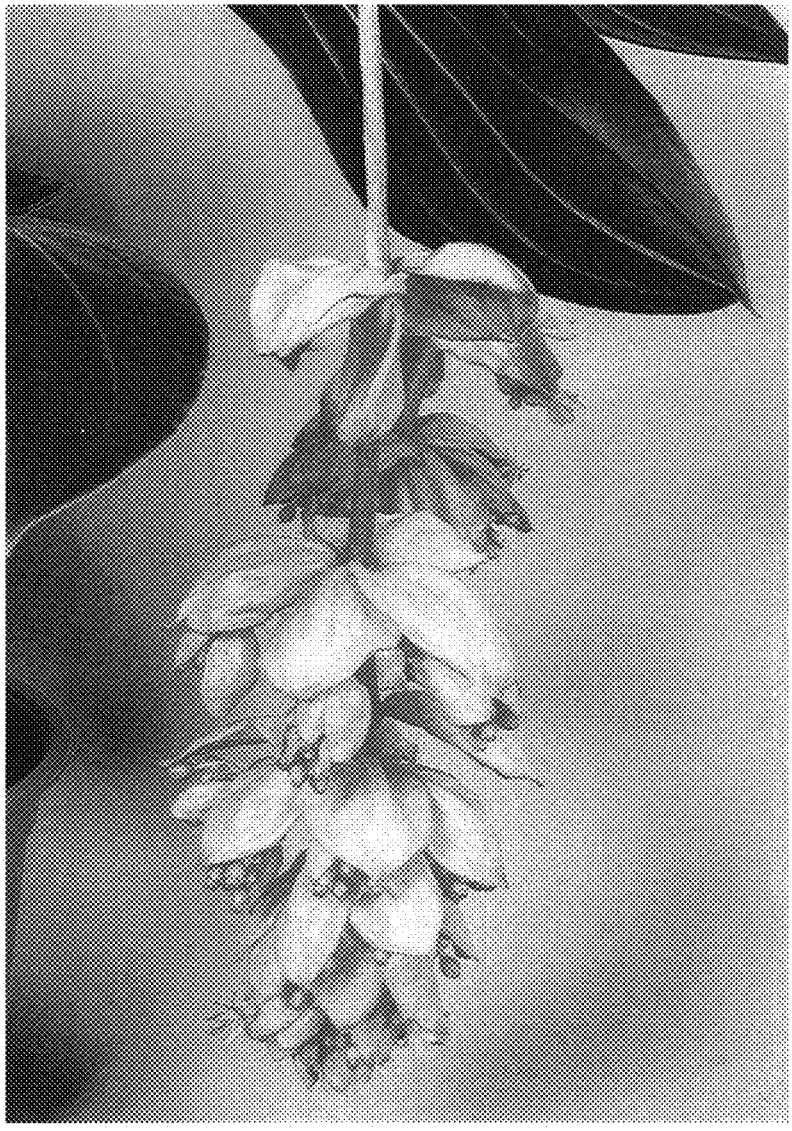

FIG. 2. shows a side view perspective of a typical inflorescence of 'ROYAL GLOW' at about 50 weeks from potting.

DETAILED BOTANICAL DESCRIPTION

'ROYAL GLOW' has not been observed under all possible environmental conditions. The phenotype of the new cultivar may vary with variations in environment such as temperature, light intensity, day length, fertilizers and humidity without any change in the genotype of the plant.

The aforementioned photograph, together with the following observations, measurements and values describe the new *Medinilla* 'ROYAL GLOW' as grown in a greenhouse in Assendelft, the Netherlands, under conditions which closely approximate those generally used in a commercial practice.

Color references are made to The Royal Horticultural Society Colour Chart (R.H.S.), 2001 Edition, except where general colors of ordinary significance are used. Color values were taken under daylight conditions in a greenhouse in Assendelft, The Netherlands. The age of the plants of 'ROYAL GLOW' described is about 50 weeks from potting.

Botanical classification: *Medinilla* hybrid 'ROYAL GLOW'.

Parentage:

*Female parent.*—*Medinilla* selection designated '88078319' (unpatented).

*Male parent.*—*Medinilla* selection designated '88078320' (unpatented).

PROPAGATION

Cuttings.

PLANT

General appearance and form:

*Height.*—About 35 cm.

*Diameter.*—About 50 cm.

*Shape.*—Erect Shrub.

*Growth habit.*—Stem.

*Plant vigor.*—Good.

*Flowering season.*—From April till October.

*Cold tolerance.*—Frost tender, temperatures below 5° C. may damage plants.

Quantity of primary lateral branches: Average: 2.

Characteristics of primary lateral branches:

*Diameter.*—About 15 mm.

*Shape.*—Winged, width of wings about 3 mm.

*Length.*—15 to 25 cm.

*Texture.*—Glabrous.

*Strength.*—Medium.

*Internode length.*—8 to 15 cm.

*Color.*—Green; near RHS 137B with lignified parts near Grey-Brown 199B.

FOLIAGE

Arrangement: Opposite.

Overall shape: Elliptical.

Quantity: About 14.

Attachment: Sessile.

Average overall length: 25 cm.

Average overall width: 13 cm.

Apex: Cuspidate.

Base: Acute.

Margin: Entire to weakly undulate.

Texture, both sides: Smooth.

Venation:

*Type.*—Sunken, below surface of leaf.

*Pattern.*—Parallel.

*Color upper side.*—Yellow-green; closest to RHS 145C.

*Color under side.*—Green; closest to RHS 138B.

INFLORESCENCE

Shape: Pendulous panicles.

Amount: About 4, depending on size of plant.

Length: Average: 42 cm.

Width: Average: 15 cm.

Aspect: Pendulous.

Color: Red, closest to RHS 62B.

Fragrance: Not observed.

Corolla:

*Number.*—About 300 per panicle.

Petals:

*Quantity.*—4-6 per flower.

*Length.*—Average: 13 mm.

*Width.*—Average: 7 mm.

*Overall shape.*—Ovate, asymmetrical.

*Apex.*—Obtuse.

*Shape.*—Obovate, symmetrical.

*Base.*—Cuneate.

*Margin.*—Entire.

*Texture.*—Glabrous all surfaces.

*Persistent or self-cleaning.*—Self-cleaning.

*Color.*—When opening, upper surface: Red-purple closest to RHS 74C. When opening, lower surface: Red-purple closest to RHS 74C.

Sepals:

*Quantity.*—Single structure identifiable, round in shape, no individual apex.

*Length.*—Maximum 8 mm.

*Width.*—Approximately 4 mm.

*Base.*—Fused.

*Margin.*—Entirely fused.

*Texture.*—Glabrous all surfaces.

*Arrangement.*—Growth together, enclosing the ovary.

*Color.*—Closest to RHS Red-Purple 62.

Bracts:

*Arrangement.*—Verticillate.

*Quantity.*—4 per crown.

*Length.*—Average 2 to 5 cm.

*Width.*—Average 1 to 3.5 cm.

*Shape.*—Elliptical.

*Color.*—Closest to Red RHS 39B.

*Apex.*—Acute.

*Base.*—Truncate.

*Margin.*—Entire.

*Texture.*—Glabrous all surfaces.

Bud:

*Length.*—Average: 10 mm.

*Diameter.*—Average: 5 mm.

*Color.*—Red-purple; near RHS 63B.

*Shape.*—Ovate.

*Texture.*—Glabrous.

Peduncles:

*Length.*—Average 16 cm.

*Diameter.*—Average 7 mm.

*Strength.*—Strong.

*Texture.*—Glabrous.

*Angle.*—Straight down.

*Color.*—Basal light green; near RHS 145C to Red-purple near RHS 59C.

Pedicels:

*Length.*—Average range 3 cm to 12 mm.

*Diameter.*—Average: 2 mm.

*Strength*.—Strong.
*Texture*.—Glabrous.
*Angle*.—About 45°.
*Color*.—Closest to Red-purple RHS 63B.

REPRODUCTIVE ORGANS

Stamens:
*Number*.—Average: 10.
*Length*.—8 mm.
*Diameter*.—<1 mm.
*Color*.—Yellow, with a white base (too small to qualify R.H.S. value).

Anthers:
*Shape*.—Basifixed, linear.
*Diameter*.—2 mm.
*Length*.—9 mm.
*Color*.—Violet, closest to RHS 83B.
*Pollen*.—Not visible.

Pistil:
*Number*.—1 per flower.
*Length*.—15 mm.
*Style*.—Length: 14 mm. Color: RHS White 155D.
*Stigma*.—Shape: Punctiform. Width: <1 mm. Color: White, too small to qualify R.H.S. value.
*Ovary*.—Shape: Obovoid. Position: Inferior. Length: 5 mm. Diameter: 3.5 mm. Color: White; closest to RHS 155C.

OTHER CHARACTERISTICS

Seeds and fruits: No seeds or fruits detected to date.
Disease/pest resistance: No observations made.
Temperature tolerance: Temperatures below 5° C. may damage plants.

What is claimed is:

1. A new and distinct cultivar of *Medinilla* plant named 'ROYAL GLOW' as herein illustrated and described.

* * * * *